United States Patent [19]
Harada

[11] Patent Number: 4,951,679
[45] Date of Patent: Aug. 28, 1990

[54] PULSE WAVE DETECTING APPARATUS HAVING PLACEMENT-CONDITION DETECTING MEANS

[75] Inventor: Chikao Harada, Nagoya, Japan

[73] Assignee: Colin Electronics Co., Ltd., Aichi, Japan

[21] Appl. No.: 299,409

[22] Filed: Jan. 23, 1989

[30] Foreign Application Priority Data

Jan. 29, 1988 [JP] Japan ................................. 63-19825

[51] Int. Cl.⁵ .............................................. A61B 5/02
[52] U.S. Cl. ..................................... 128/672; 128/687; 128/688
[58] Field of Search .............................. 128/687-690, 128/639, 672, 666, 736

[56] References Cited

U.S. PATENT DOCUMENTS

| | | | |
|---|---|---|---|
| 4,129,124 | 12/1978 | Thalman | 128/690 X |
| 4,294,263 | 10/1981 | Hochman | 128/736 |
| 4,295,475 | 10/1981 | Torzala | 128/736 |
| 4,307,727 | 12/1981 | Haynes | 128/690 X |
| 4,331,161 | 5/1982 | Patel | 128/736 |
| 4,660,566 | 4/1987 | Palti | 128/677 |

FOREIGN PATENT DOCUMENTS 0122123 10/1984 European Pat. Off. .
0182197 5/1986 European Pat. Off. .
3008601 9/1981 Fed. Rep. of Germany .

OTHER PUBLICATIONS

Laid-Open Publication 63-201510.

Primary Examiner—Francis Jaworski
Attorney, Agent, or Firm—Oliff & Berridge

[57] ABSTRACT

A pulse wave detecting apparatus having a housing which is placed on a body surface of a subject such that the housing is aligned with an artery of the subject via the body surface, a pulse wave sensor accommodated in the housing, the pulse wave sensor being pressed against the body surface for detecting pulse wave produced from the artery, and a pressing device supported by the housing, the pressing means pressing the pulse wave sensor against the body surface with an optimum pressing force, the optimum pressing force being determined based on pulse wave signal produced by the pulse wave sensor while the pressing force of the pressing means is varied, the apparatus including a detecting device for detecting whether or not the housing has been placed on the body surface of the subject.

7 Claims, 4 Drawing Sheets

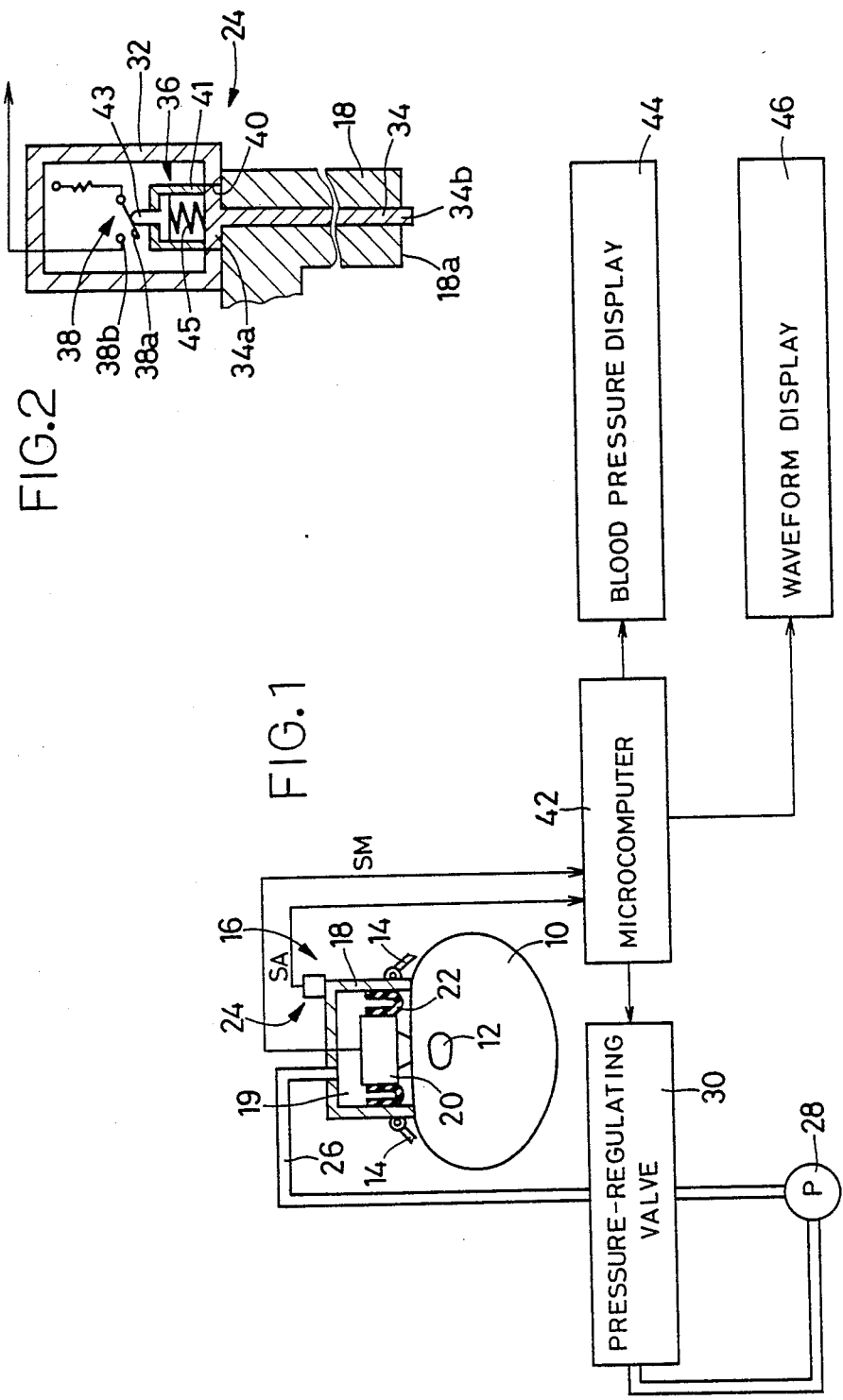

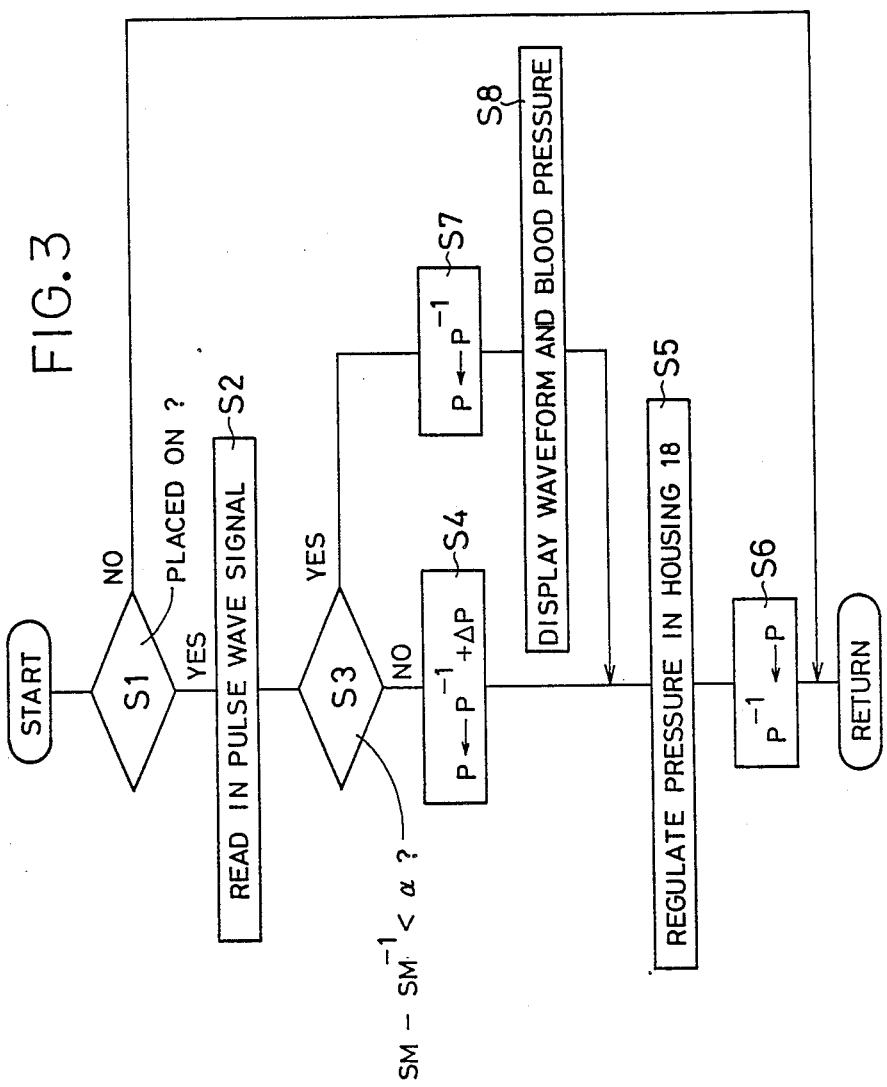

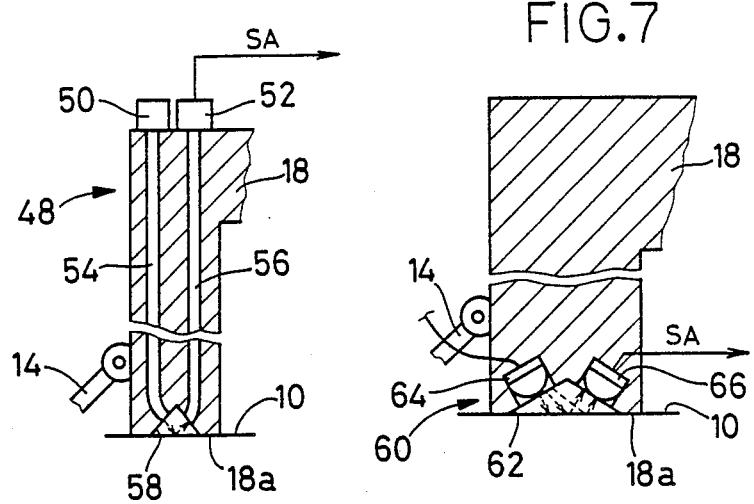
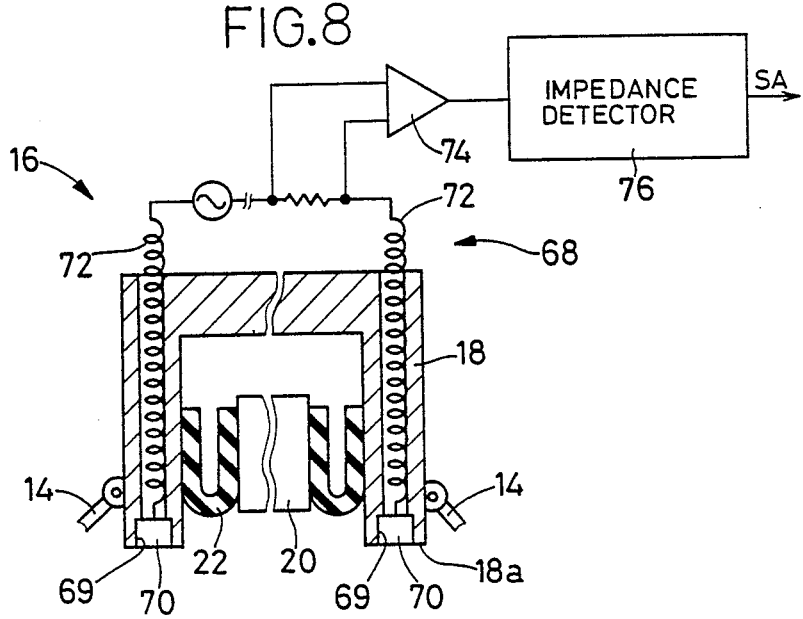

PULSE WAVE DETECTING APPARATUS HAVING PLACEMENT-CONDITION DETECTING MEANS

BACKGROUND OF THE INVENTION

1. Field of the Invention

The present invention relates to improvements in an apparatus for detecting pulse wave produced from an arterial vessel of a living body.

2. Related Art Statement

The Assignee to which the present U.S. patent application is assigned, previously filed Japanese Utility Model Application No. 62-93846 on June 18, 1987 in which they disclose a pulse wave detecting apparatus having (a) a pulse wave sensor which is pressed against a body surface over an arterial vessel so as to detect pulse wave produced from the artery, and (b) pressing means for pressing the pulse wave sensor against the body surface with an optimum pressing force, the optimum pressing force being determined based on pulse wave signal produced by the pulse wave sensor while the pressing force of the pressing means is varied, so that the magnitude of the pulse wave signal is optimized.

The above pulse wave detecting apparatus operates normally so that the pressing force of the pressing means is optimized, on the condition that the pulse wave sensor has already been placed on the body surface of a subject. However, if the pressing means is activated to press the pulse wave sensor though the sensor has not been contacted with the body surface, the pressing means is operated until pulse wave signal is produced from the sensor. In such case, the pulse wave sensor is displaced an excessively large operation amount or stroke by the pressing means. This tends to cause a mechanical breakdown or failure in the apparatus.

SUMMARY OF THE INVENTION

It is therefore an object of the present invention to provide a pulse wave detecting apparatus characterized by having means for detecting whether or not the housing thereof accommodating the pulse wave sensor thereof and supporting the pressing means thereof, has been placed on a body surface of a subject.

The above object has been achieved by the present invention, which provides a pulse wave detecting apparatus having (a) a housing which is placed on a body surface of a subject such that the housing is aligned with an artery of the subject via the body surface, (b) a pulse wave sensor accommodated in the housing, the pulse wave sensor being pressed against the body surface for detecting pulse wave produced from the artery, and (c) pressing means supported by the housing, the pressing means pressing the pulse wave sensor against the body surface with an optimum pressing force, the optimum pressing force being determined based on pulse wave signal produced by the pulse wave sensor while the pressing force of the pressing means is varied, the apparatus comprising (d) detecting means for detecting whether or not the housing has been placed on the body surface of the sujbect.

In the pulse wave detecting apparatus constructed as described above, the detecting means detects whether or not the pulse wave sensor and pressing means have been held in place the body surface of the subject. Accordingly, the pressing means is protected from erroneously being operated though the sensor and pressing means have not been contacted with the body surface, for example when an ON/OFF switch is erroneously turned on to activate the pressing means. Therefore, the present pulse wave detecting apparatus is free from the problem that the pressing means is operated by an excessively large operation amount, or the mechanical breakdown resulting from that problem.

In a preferred embodiment of the pulse wave detecting apparatus of the present invention, the detecting means comprises a displaceable member slidably held by the housing such that a portion of the displaceable member normally protrudes from a surface of the housing which surface contacts the body surface when the housing is placed on the body surface, and a detector switch for detecting displacement of the displaceable member, the detector switch generating a placement signal representing that the housing is placed on the body surface, when detecting the displacement of the displaceable member.

In another embodiment of the apparatus of the invention, the detecting means comprises a light emitter supported by the housing for emitting light beam toward the body surface of the subject, and a light detector supported by the housing for detecting the light beam reflected by the body surface, the light detector generating a placement signal representing that the housing is placed on the body surface, when detecting the light beam reflected by the body surface. In this embodiment, it is preferred that the detecting means further comprise a first optical fiber for transmitting the light beam from the light emitter toward the body surface, and a second optical fiber for transmitting the light beam reflected by the body surface to the light detector.

In yet another embodiment of the apparatus of the invention, the detecting means comprises a pair of electrodes held in a surface of the housing which surface contacts the body surface when the housing is placed on the body surface, and an impedance detector for detecting an impedance between the pair of electrodes, the impedance detector generating, based on the detected impedance, a placement signal representing that the housing is placed on the body surface.

According to a preferred feature of the present invention, the pulse wave detecting apparatus further comprises inhibiting means for inhibiting the pressing means from pressing the pulse wave sensor, while the placement signal is not generated by the detecting means.

According to another feature of the present invention, the pulse wave detecting apparatus further comprises permitting means for permitting the pulse wave sensor to be subjected to zero adjustment, while the placement signal is not generated by the detecting means. In this case, the zero adjustment of the pulse wave sensor is performed only on the condition that the sensor and pressing means are not placed on the body surface of the subject. Thus, the zero adjustment of the pulse wave sensor is free from influence from the subject. This assures accurate zero adjustment of the pulse wave sensor.

According to yet another feature of the present invention, the pulse wave detecting apparatus further comprises permitting means for permitting generation of an aberrant signal representing that the pulse wave signal from the pulse wave sensor is aberrant, while the placement signal is generated by the detecting means. When the magnitude of the pulse wave signal has fallen below a predetermined value, for example, an aberrant signal is generated for example to activate an alarm device so as to inform the medical staff of the aberration of the subject. In this apparatus, however, no aberrant signal is generated while the housing (pulse wave sensor and pressing means) is not placed on the body surface, namely, so long as the housing is located apart from the subject. Therefore, the apparatus is free from a problem that alarming sound is erroneously produced as a result of confusion between the aberrant signal representing the aberrant pulse wave and slight oscillation (pressure variation) detected by the pulse wave sensor spaced apart from the subject.

BRIEF DESCRIPTION OF THE DRAWINGS

The above and optional objects, features and advantages of the present invention will be better understood by reading the following detailed description of the presently preferred embodiments of the invention, when considered in conjunction with the accompanying drawings, in which:

FIG. 1 is an illustrative view showing a general construction of a pulse wave detecting apparatus of the present invention;

FIG. 2 is an enlarged cross-sectional view of a switch device of the apparatus of FIG. 1;

FIG. 3 is a flow chart showing the operation of the apparatus of FIG. 1;

FIGS. 6 through 8 are enlarged cross-sectional views of modified switch devices employed in the pulse wave detecting apparatus of the invention.

DETAILED DESCRIPTION OF THE PREFERRED EMBODIMENTS

Figure 4:
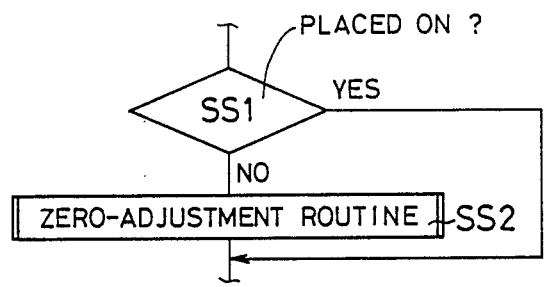
FIGS. 4 and 5 are flow charts partially showing the operation of other embodiments of the pulse wave detecting apparatus of the invention.

Referring first to FIG. 1, there is shown a pulse wave detecting apparatus embodying the present invention. In the figure, reference numeral 10 designates a body surface of a subject, for example, the surface of an upper arm. An arterial vessel 12 extends along the body surface 10. Right above the artery 12 a pulse wave detecting probe 16 is fixed with a band 14 fastened around the upper arm.

The pulse wave detecting probe 16 includes a rectangular box-like housing 18, a pulse wave sensor 20 accommodated in the housing 18, a generally annular rubber diaphragm 22 and a switch device 24. The housing 18 is open at a bottom end thereof as viewed in FIG. 1 and is formed of comparatively rigid material. The pulse wave sensor 20 consists of a pressure-sensitive semiconductor element, for example. The diaphragm 22 is disposed between the housing 18 and the pulse wave sensor 20 such that the diaphragm 22 secures the sensor 20 to the housing 18, and such that the diaphram 22 cooperates with the housing 18 and sensor 20 to define a fluid-tight space 19 in the housing 18. The fluid-tight space 19 communicates with an electrically operated pump 28 via a pipe 26 and a pressure-regulating valve 30 which is operated under control of a microcomputer 42 (described below in detail). The space 19 is supplied with a pressurized fluid from the pump 28 whose pressure is regulated by the valve 30. More specifically described, as the pressurized fluid is supplied from the pump 28 to the fluid-tight space 19, pressure level in the space 19 is progressively increased and the diaphragm 22 is inflated or swollen toward the body surface 10. Consequently, the pulse wave sensor 20 is pressed against the body surface 10. The sensor 20 detects pulse wave of the artery 12, namely, oscillatory pressure wave of the artery 12 which is produced by expansion and contraction of the artery 12 synchronized with heart beat of the subject, and generates pulse wave signal SM representing the detected pulse wave, to the microcomputer 42. In the present embodiment, the diaphragm 22 serves as the pressing means of the pulse wave detecting apparatus.

Referring next to FIG. 2, there is illustrated the switch device 24. The switch device 24 includes a casing 32, a displaceable member 34, an actuator 36 and an ON/OFF switch 38. The casing 32 is fixed to an upper surface of the housing 18. The displaceable member 34 extends through a side wall of the housing 18 such that the displaceable member 34 is slidable vertically as viewed in FIG. 1. The displaceable member 34 has a flanged head 34a. The actuator 36 is fixed to an upper surface of the flanged head 34a of the displaceable member 34. The ON/OFF switch 43 is secured immovable to an inner wall surface of the casing 32 by fastening members (not shown), and has a pair of terminals 38a, 38b one of which 38a is in contact with the actuator 36. As shown in FIG. 2, while the pulse wave detecting probe 16 (housing 18) is not placed on the body surface 10, namely, is spaced apart from the subject, the displaceable member 34 is placed at a non-displacement position thereof in which the flanged head 34a thereof is in contact with the upper surface of the housing 18 and is fitted in an opening 40 formed through a bottom wall of the casing 32 and a free end 34b of a leg portion of the displaceable member 34 protrudes from a bottom surface 18a of the housing 18 which surface contacts the body surface 10 when the probe 14 is placed on the body surface 10. The actuator 36 includes a box-like member 41 which is fixed to the upper surface of the displaceable member 34 (flanged head 34a) and is open at an bottom end thereof, a contact member 43 which is accommodated in the box-like member 41 and partially protrudes outward through an upper wall of the box-like member 41, and a spring 45 disposed between the contact member 43 and the head 43a of the displaceable member 43.

If the pulse wave detecting probe 16 is fastened around the upper arm of the subject and the housing 18 is held in place on the body surface 10, the free end 34b of the leg portion of the displaceable member 34 protruding from the bottom surface of the housing 18, is pressed and displaced inward as a result of contact with the body surface 10, and the above-indicated one terminal 38a contacting the actuator 36 is closed by the displacement of the displacement member 34. Thus, the switch 38 generates from the other terminal 38b a displacement signal SA representing that the probe 16 is placed on the body surface 10, to the microcomupter 42. In the present invention, the switch device 24 serves as the placement-condition detecting means for detecting whether or not the probe 16 (housing 18) has been placed on the body surface 10 of the subject. The spring 45 serves to accommodate an excessive displacement or stroke of the displaceable member 34, thereby contributing to protect the switch 38 from mechanical damage.

The microcomputer 42 includes a CPU (central processing unit), a RAM (random access memory), a ROM (read only memory) and an I/O interface (all not shown), and the CPU processes the input signals according to programs stored in the ROM by utilizing the temporary-storage function of the RAM, and controls the pressure-regulating valve 30 to regulate the pressure level of the pressurized fluid in the fluid-tight space 19 in the housing 18. More specifically described, upon operation of a START button (not shown), the microcomputer 42 activates the valve 30 to allow the pressurized fluid to be supplied from the electric pump 28 to the fluid-tight space 19. Subsequently the microcomputer 42 calculates the magnitude of the pulse wave signal SM, for example the amplitude or electric power of the signal SM, and thereby determines whether or not the magnitude of the signal SM has been saturated. If the signal SM has been saturated, the microcomputer 42 commands the pressure-regulating valve 30 to maintain the current pressure level in the space 19. This process is performed by feed back control.

The CPU of the microcomputer 42 determines blood pressure of the subject based on the pulse wave signal SM, and commands a blood pressure display 44 to indicate the thus-determined blood pressure and concurrently commands a waveform display 36 to indicate the waveform of the pulse wave represented by the signal SM. Since an upper peak value of the pulse wave corresponds to a maximum blood pressure and a lower peak value of the pulse wave corresponds to a minimum blood pressure, actual blood pressure indicated by the blood pressure display 44 is determined according to a pre-determined relationship between the pulse wave and the blood pressure and based on the actual upper and lower peak values of the pulse wave represented by the signal SM. Further, the waveform of the pulse wave indicated by the waveform display 36 represents variation in arterial pulse pressure, which provides clinically or medically important information. One of the blood pressure display 44 and the waveform display 46 may be omitted.

The CPU of the microcomputer 42 continues to measure the blood pressure by utilizing the pulse wave signal SM, while the microcomputer 42 receives the placement signal SA from the switch device 24. However, while the microcomputer 42 does not receive the signal SA, namely, while the pulse wave detecting probe 16 is not placed on the body surface 10, the microcomputer 42 inhibits the pressure-regulating valve 30 from supplying the fluid-tight space 19 in the housing 18 with the pressurized fluid from the electric pump 28.

There will be described the operation of the pulse wave detecting apparatus constructed as illustrated above, in conjuction with the flow chart of FIG. 3.

Upon operation of the START button (not shown), initially the CPU of the microcomputer 42 executes step S1 at which it is judged whether or not the placement signal SA is generated by the switch device 24, namely, whether or not the pulse wave detecting probe 16 has been placed on the body surface 10. If the judgement at step S1 is negative, namely, if it is judged that the probe 16 has not been placed on the body surface 10, the CPU control again executes step S1. On the other hand, if the judgement at step S1 is affirmative, namely, if it is judged that the probe 16 has been placed on the body surface 10, step S1 is followed by step S2 at which the CPU reads in the pulse wave signal SM supplied from the pulse wave sensor 20. At the following step S3, it is judged whether or not the difference between the amplitude of the currently read-in pulse wave signal SM and that of the preceding pulse wave signal $SM^{-1}$, namely $(SM-SM^{-1})$, is smaller than a predetermined very small value $\alpha$. Step S3 is provided for determining whether or not the magnitude of the pulse wave signal has been saturated, based on the fact that, once the pulse wave signal is saturated, the difference between the amplitudes of the successive two signals $SM^{-1}$ and SM does not exceed the very small value $\alpha$. At the beginning of the operation the magnitude of the pulse wave signal has not been saturated yet. Accordingly, the judgement at step S3 is found to be negative. Thus, step S3 is followed by steps S4 through S6. At step S4 the CPU adds a comparatively small value $\Delta P$ to a fluid pressure $P^{-1}$ in the fluid-tight space 19 which has been stored in the RAM of the microcomputer 42 for the current pulse wave detecting cycle, so as to determine a target fluid pressure P to be used for detecting the following pulse wave signal. At the following step S5 the CPU controls the pressure-regulating valve 30 to increase the fluid pressure in the fluid-tight space 19 from the stored value $P^{-1}$ to the target value P, and at step S6 the CPU stores the new value P in the RAM in place of the previous value $P^{-1}$ for the following pulse wave detecting cycle. As shown in the flow chart of FIG. 3, the new value P is stored as $P^{-1}$ in the RAM. As steps S1 through S6 are repeated, the fluid pressure P in the space 19 is increased little by little, namely, by $\Delta P$ for each cycle. In this process, if the judgement at step S3 is turned to be affirmative, namely, if the magnitude of the pulse wave signal SM is saturated, step S3 is followed by steps S7 and S8. At step S7 the CPU determines the pressure $P^{-1}$ used in the current cycle, as a target pressure P to be used for the following pulse wave detecting cycle, without adding the small value $\alpha$ to the pressure $P^{-1}$. Step S7 is followed by step S8 at which the waveform of the pusle wave represented by the signal SM read in at step S2, is displayed on the waveform display 46 and concurrently the maximum and minimum blood pressure is determined based on the pulse wave signal SM and displayed on the blood pressure display 44. At the following step S5 the CPU controls the pressure-regulating valve 30 to maintain the fluid pressure P in the fluid-tight space 19 in the housing 18 and at step S6 the CPU stores the value P as $P^{-1}$ in the RAM.

As is apparent from the foregoing, in the present embodiment, at step S1 it is judged whether or not the pulse wave detecting probe 16 has been placed on the body surface 10, and if the judgement at step S1 is negative, the pulse wave sensor 20 is by no means pressed against the body surface 10 by the diaphragm 22, namely, the diaphragm 22 is not inflated by the pressurized fluid from the electric pump 28. Accordingly, even if the START button is erroneously operated though the probe 16 (sensor 20) has not been held in place on the body surface 10, the pressurized fluid is not supplied to the fluid-tight space 19 in the housing 18. Thus, the instant apparatus has overcome the problem that the pulse wave sensor 20 is displaced beyond its permissible operation amount or stroke though the sensor 20 has not been placed on the body surface 10, and the problem of the mechanical breakdown or failure of the apparatus due to the excessive displacement of the sensor 20.

There will be described below other embodiments of the pulse wave detecting apparatus of the present invention.

In one embodiment, the pulse wave detecting apparatus is operated according to the flow chart of FIG. 4 which includes the same steps as those of the flow chart of FIG. 3 except for step S1, and a sub-routine consisting of steps SS1 and SS2 in place of step S1 of FIG. 3.

The sub-routine is executed in an initialization process of the apparatus. More specifically described, at step SS1 it is judged whether or not a placement signal SA is present, namely, whether or not the probe 16 has been placed on the body surface 10, similar to step S1 of the embodiment of FIG. 3. If the judgement at step SS1 is affirmative, the same operations as indicated at steps S2 and the following of FIG. 3 are executed. On the other hand, if the judgement at step SS1 is negative, step SS1 is followed by step SS2 at which a zero-adjustment routine is performed. The zero-adjustment routine is provided for adjusting a zero point of the pulse wave sensor 20 (for example, pressure-sensitive semiconductor element). The zero adjustment is conducted by eliminating any drift of the zero point of the sensor 20. In other words, the sensor 20 is re-calibrated. Thus, the detection accuracy of the sensor 20 is maintained high. The zero adjustment of the sensor 20 is required to be performed while the sensor 20 is not pressed against the body surface 10, namely, while the sensor 20 is detecting atmospheric pressure. Step SS2 is followed by the same steps as steps S2–S8 of the embodiment of FIG. 3. The zero-adjustment routine of step SS2 is performed only in the case where the judgement at step SS1 is negative, namely, while the pulse wave detecting probe 16 is not placed on the body surface 10. Thus, the zero adjustment (re-calibration) of the pulse wave sensor 20 is performed in a reliable manner.

Figure 5:
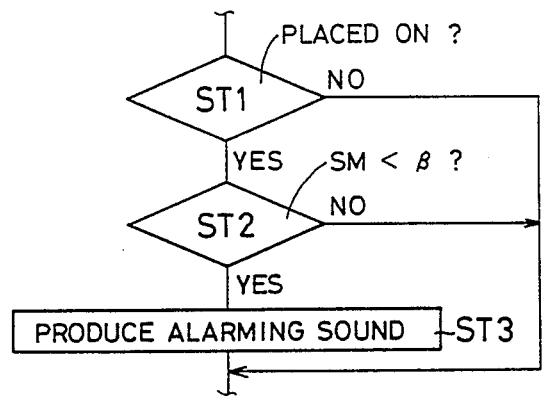

In another embodiment of FIG. 5, the pulse wave detecting apparatus has a construction similar to that of the embodiment of FIG. 1, but is different therefrom in that an alarm device (not shown) is coupled to a CPU of a microcomputer 42 of the instant apparatus. When the CPU detects that the pulse wave signal SM is aberrant, and generates an aberrant signal, the alarm device is activated to produce alarming sound so as to inform the medical staff of the aberration of the subject. The instant apparatus is operated according to a flow chart consisting of a main routine which includes the same steps as those of the flow chart of FIG. 3 except for step S1, and a sub-routine which is inserted between appropriate successive steps and includes steps ST1, ST2 and ST3. At step ST1 it is judged whether or not a placement signal SA is present, namely, whether or not a pulse wave detecting probe 16 is placed on a body surface of a subject. If the judgement at step ST1 is negative, the control of the CPU returns to the main routine. On the other hand, if the judgement at step ST1 is affirmative, step ST1 is followed by step ST2 at which it is judged whether or not the amplitude of the pulse wave signal SM is smaller than a pre-determined value $\beta$. The value $\beta$ is pre-determined to be considerably small as compared with a normal amplitude of the pulse wave signal SM. Accordingly, if the amplitude of the pulse wave signal SM supplied from the sensor 20 is smaller than the value $\beta$, it is judged that the signal SM is aberrant (or abnormal), namely, that the pulse wave of the subject is aberrant. If the judgement at step ST2 is thus found to be affirmative, the CPU generates an aberrant signal to the alarm device (not shown). At the following step ST3, the alarm device responds to the aberrant signal to produce alarming sound.

In the embodiment of FIG. 5, the CPU permits generation of the aberrant signal representing that the pulse wave signal SM is aberrant, only while the pulse wave detecting probe 16 is placed on the body surface 10 of the subject. Thus, the instant pulse wave detecting apparatus is free from the problem that alarming sound is erroneously produced though the probe 16 is not held in place on the body suface 10 as a result of confusion between aberrant pulse wave and slight oscillation (pressure variation) detected by the sensor 20 spaced apart from the body surface 10.

While the present invention has been described with detailed particularities of the presently preferred embodiments, it is to be understood that the invention may be embodied with various modifications.

While in the illustrated embodiment of FIG. 1 the switch device 24 is constructed to utilize mechanical displacement of the displacement member 34 for detecting that the pulse wave detecting probe 16 is placed on the body surface 10, it is possible to employ a switch device 48 of an optical type as shown in FIG. 6, in place of the mechanical switch device 24. The optical switch device 48 includes a light emitter 50 and a light detector 52 both of which are secured to the upper surface of the housing 18, and a pair of first and second optical fibers 54, 56 which are connected to the light emitter 50 and the light detector 52, respectively, and extend through a side wall of the housing 18. A recess 58 having a V-shaped profile in cross section is formed in a bottom surface 18a of the side wall of the housing 18 which surface contacts the body surface 10 when the probe 16 is placed on the body surface 10. The first optical fiber 54 connected at one end thereof to the light emitter 50, is exposed at the other end thereof in a tapered surface of the recess 58. Similarly, the second optical fiber 56 connected at one end thereof to the light detector 52, is exposed at the other end thereof in the tapered surface of the recess 58. When the probe 16 is placed on the body surface 10 and the light emitter 50 is activated to emit light beam, the first optical fiber 54 transmits the light beam from the light emitter 50, and emits the light beam at the recess 58 toward the body surface 10. The second optical fiber 56 transmits the light beam reflected by the body surface 10, to the light detector 52. Upon detection of the light beam, the light detector 52 generates a placement signal SA representing that the probe 16 is placed on the body surface 10, to the microcomputer 42 (CPU). Thus, the CPU of the microcomputer 42 detects that the probe 16 is placed on the body surface 10.

Furthermore, it is possible to use a switch device 60 as shown in FIG. 7 in place of the switch device 24 of FIG. 2 or the switch device 48 of FIG. 6. The switch device 60 includes a light emitter 64 and a light detector 66 both of which are embedded in a side wall of the housing 18 and exposed in a recess 62 formed in a bottom surface 18a of the side wall of the housing 18 which surface contacts the body surface 10 when the probe 16 is placed on the body surface 10. The recess 62 has a tapered surface, and a V-shaped profile in cross section, like the recess 58 of FIG. 6. The light emitter 64 is coupled to a light source (not shown), and emits light beam from the tapered surface of the recess 62 toward the body surface 10. The light detector 64 detects the light beam reflected by the body surface 10. When the pulse wave detecting probe 16 is placed on the body surface 10, the light beam emitted from the light emitter 64 is reflected by the body surface 10 and detected by the light detector 66. Upon detection of the light beam reflected by the body surface 10, the light detector 66 generates a placement signal SA to the microcomputer 42, similar to the light detector 52 of the switch device 48 of FIG. 6.

Referring to FIG. 8, there is shown another switch device 68 which is used in place of the switch devices 24, 48, 60 of FIGS. 2, 6, 7. The switch device 68 is adapted to detect that the pulse wave detecting probe 16 is placed on the body surface 10, by utilizing impedance of the body surface or skin 10. The switch device 68 includes a pair of electrodes 70, 70 embedded in a pair of cavities 69, 69 formed in a pair of opposed side walls of the housing 18. More specifically described, the pair of cavities 69, 69 are formed in a bottom surface 18a of the housing 18 which surface contacts the body surface 10 when the probe 16 is placed on the body surface 10. A small current is applied between the pair of electrodes 70, 70. With the probe 16 placed on the body surface 10, the pair of electrodes 70, 70 contact the body surface 10. When the pair of electrodes 70, 70 contact the body surface 10, an impedance of the body surface 10 between the electrodes 70, 70 is detected by an impedance detector 76 through a pair of wirings 72 and an amplifier 74. Upon detection of the impedance of the body surface 10, the impedance detector 76 of the switch device 68 generates a placement signal SA to the microcomputer 42.

It is to be understood that the present invention may be embodied with other changes, improvements and modifications which may occur to those skilled in the art without departing from the scope and spirit of the invention defined in the appended claims.

What is claimed is:

1. A pulse wave detecting apparatus comprising:
a housing which is adapted to be placed on a body surface of a subject;
a pulse wave sensor supported by said housing, for detecting a pulse wave produced from an artery of said subject;
pressing means supported by said housing, for pressing said pulse wave sensor against said body surface so as to detect said pulse wave;
control means for determining an optimum pressing force of said pressing means applied to said pulse wave sensor, based on the pulse wave detected by said pulse wave sensor as the pressing force of said pressing means is varied, and maintaining the optimum pressing force;
detecting means for detecting whether or not said housing is placed on said body surface of said subject, said detecting means generating a placement signal when detecting that said housing is placed on said body surface; and
inhibiting means for inhibiting said pressing means from pressing said pulse wave sensor, when said placement signal is not generated by said detecting means.

2. The apparatus as recited in claim 1, wherein said detecting means comprises:
a displaceable member slidably held by said housing such that a portion of said displaceable member normally protrudes from a surface of said housing which surface contacts said body surface when said housing is placed on said body surface; and
detector switch means for detecting displacement of said displaceable member, said detector switch means generating a placement signal representing that said housing is placed on said body surface, when detecting said displacement of said displaceable member.

3. The apparatus as set forth in claim 1, wherein said detecting means comprises:
light emitter means, supported by said housing, for emitting a light beam toward said body surface of said subject, said light beam being reflected by said body surface; and
light detector means, supported by said housing, for detecting said light beam reflected by said body surface, said light detector means generating a placement signal representing that said housing is placed on said body surface, when detecting said light beam reflected by said body surface.

4. The apparatus as set forth in claim 3, wherein said detecting means further comprises:
a first optical fiber for transmitting said light beam from said light emitter means toward said body surface; and
a second optical fiber for transmitting said light beam reflected by said body surface to said light detector means.

5. The apparatus as set forth in claim 1, wherein said detecting means comprises:
a pair of electrodes held in a surface of said housing which surface contacts said body surface when said housing is placed on said body surface; and
an impedance detector means for detecting an impedance between said pair of electrodes, said impedance detector means generating, based on the detected impedance, a placement signal representing that said housing is placed on said body surface.

6. The apparatus as set forth in claim 1, further comprising permitting means for permitting said pulse wave sensor to be subjected to zero adjustment, while said placement signal is not generated by said detecting means.

7. The apparatus as set forth in claim 1, further comprising permitting means for permitting generation of an aberrant signal representing that said pulse wave signal from said pulse wave sensor is aberrant, while said placement signal is generated by said detecting means.

* * * * *